US010722164B2

(12) United States Patent
Chatterjee et al.

(10) Patent No.: US 10,722,164 B2
(45) Date of Patent: Jul. 28, 2020

(54) METHOD AND SYSTEM FOR DETECTION AND ANALYSIS OF COGNITIVE FLOW

(71) Applicant: Tata Consultancy Services Limited, Mumbai (IN)

(72) Inventors: Debatri Chatterjee, Kolkata (IN); Aniruddha Sinha, Kolkata (IN); Meghamala Sinha, Kolkatta (IN); Sanjoy Kumar Saha, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 15/756,576

(22) PCT Filed: Mar. 22, 2017

(86) PCT No.: PCT/IB2017/051649
§ 371 (c)(1),
(2) Date: Feb. 28, 2018

(87) PCT Pub. No.: WO2017/221082
PCT Pub. Date: Dec. 28, 2017

(65) Prior Publication Data
US 2019/0110726 A1    Apr. 18, 2019

(30) Foreign Application Priority Data

Jun. 24, 2016    (IN) .............................. 201621021811

(51) Int. Cl.
*A61B 5/16* (2006.01)
*A61B 5/00* (2006.01)
(Continued)

(52) U.S. Cl.
CPC .............. *A61B 5/16* (2013.01); *A61B 5/0205* (2013.01); *A61B 5/02405* (2013.01);
(Continued)

(58) Field of Classification Search
CPC .. A61B 5/0533; A61B 5/0476; A61B 5/02405
See application file for complete search history.

(56) References Cited

U.S. PATENT DOCUMENTS 6,947,790 B2 * 9/2005 Gevins ................. A61B 5/0484
600/544
7,720,779 B1 * 5/2010 Perry ..................... G06N 7/005
706/45
(Continued)

FOREIGN PATENT DOCUMENTS

WO    WO-2015/027079    2/2015

OTHER PUBLICATIONS

Heckerman, David. "A Tutorial on Learning with Bayesian Networks." Innovations in Bayesian Networks, SCI 156, 2008, pp. 33-82 (Year: 2008).*
(Continued)

*Primary Examiner* — Gary Jackson
*Assistant Examiner* — Anant A Gupta
(74) *Attorney, Agent, or Firm* — Finnegan, Henderson, Farabow, Garrett & Dunner LLP

(57)    ABSTRACT

A system and method for detection and analysis of learner's/performers cognitive flow have been provided. The system is configured to measure the cognitive state of the performer, while they are performing tasks of various complexity levels, using physiological responses like brain activation, heart rate variability and galvanic skin response. The system uses a Bayesian network based framework to probabilistically evaluate the cognitive state of the learner from the difficulty levels of the tasks, IQ level of the learner and observations made using the physiological sensing. The system also measures the actual cognitive state using a questionnaire. The predicted cognitive state and the actual
(Continued)

cognitive state is compared and based on the outcome of comparison a relevant step is taken.

11 Claims, 12 Drawing Sheets

(51) Int. Cl.
    *A61B 5/0205*     (2006.01)
    *A61B 5/024*     (2006.01)
    *A61B 5/053*     (2006.01)
    *A61B 34/10*     (2016.01)
    *A61B 5/048*     (2006.01)
    *G16H 50/30*     (2018.01)
    *G16H 10/20*     (2018.01)
    *G16H 50/50*     (2018.01)
    *A61B 5/0476*     (2006.01)

(52) U.S. Cl.
    CPC .......... *A61B 5/02416* (2013.01); *A61B 5/048* (2013.01); *A61B 5/0476* (2013.01); *A61B 5/0533* (2013.01); *A61B 5/165* (2013.01); *A61B 5/4884* (2013.01); *A61B 5/7264* (2013.01); *A61B 5/7275* (2013.01); *A61B 34/10* (2016.02); *G16H 10/20* (2018.01); *G16H 50/30* (2018.01); *G16H 50/50* (2018.01); *A61B 2503/12* (2013.01); *A61B 2505/09* (2013.01)

(56) References Cited

U.S. PATENT DOCUMENTS

| | | | | |
|---|---|---|---|---|
| 8,041,632 | B1* | 10/2011 | Coleman | G06Q 30/0202 705/38 |
| 9,367,666 | B2* | 6/2016 | Shankle | A61B 5/165 |
| 2012/0215450 | A1* | 8/2012 | Ashok | G05B 23/0254 702/9 |
| 2013/0144537 | A1* | 6/2013 | Schalk | G06F 15/00 702/19 |
| 2015/0066104 | A1* | 3/2015 | Wingeier | A61N 2/006 607/45 |
| 2018/0192936 | A1* | 7/2018 | Widge | G16H 15/00 |
| 2019/0113973 | A1* | 4/2019 | Coleman | G06N 5/046 |

OTHER PUBLICATIONS

Screen captures from YouTube video clip entitled "Test TOL-F Tower of London—Freiburg Version (Vienna Test System)," 4 pages, uploaded on Aug. 13, 2013 by user "SchuhfriedGmbH". Retrieved from Internet: <https://www.youtube.com/watch?v=TO3WtNQvjSo>. (Year: 2013).*

Heckerman, David. "A Tutorial on Learning with Bayesian Networks." Learning in Graphical Models, 1998, pp. 301-354 (Year: 1998).*

* cited by examiner

METHOD AND SYSTEM FOR DETECTION AND ANALYSIS OF COGNITIVE FLOW

CROSS-REFERENCE TO RELATED APPLICATIONS AND PRIORITY

This application is a U.S. National Stage Filing under 35 U.S.C. § 371 and claims priority from International Application No. PCT/IB2017/051649, filed on Mar. 22, 2017, which claims priority from India Application No. 201621021811, filed on Jun. 24, 2016. The entire contents of the aforementioned application are incorporated herein by reference.

TECHNICAL FIELD

The present application generally relates to the analysis of a learner's/performers cognitive flow. More particularly, but not specifically, the invention provides a method and system for detection and analysis of learner's cognitive flow using physiological sensors and Bayesian network based framework.

BACKGROUND

In psychology, cognitive flow is a state of mind involving complete attention with a sense of enjoyment. A person's skill and the challenge of a task together result in different emotional states. When skill is too low and the task too challenging, people become anxious. Alternatively, if the task is too easy and skill is comparatively higher, people become bored. However, when the skill and the challenge are relatively proportional, people enter in a flow state, i.e. state of focused concentration and enjoyment.

It is very challenging to provide a learning experience to a person such as a student or a working professional in which a steady cognitive flow state is maintained i.e. which is meaningful, motivated and at the same time enjoyable in nature. This often affects the students who cannot learn or do not want to learn due to lack of engagement or guidance. The same is also true for the working professional in industries. It is very necessary to provide steady flow state to a learner. Further, it is also important to know the mental state of the person in order to maintain the optimum level of performance.

The mental state of an individual varies according to their IQ levels, task difficulties or other psychological or environmental reasons. The skill level of an individual is directly related to his or her IQ level and is treated as the prior knowledge of the individual. On the other hand, the challenge of the task is synonymous to the task difficulty level.

There are different approaches for measuring the flow state mainly indirect and direct approach. Indirect approach involves namely, (i) semi-structured interviews—for measuring a qualitative performance, (ii) questionnaires—flow state questionnaires/scales used to describe user experience and performance, (iii) experience sampling method—objective is to measure flow and other states of consciousness occurring in activities encountered in everyday life. The other indirect approach involve flow measurement in different domains like piano playing, video-game, online games, social networking sites, e-commerce business etc. These indirect approaches seem to be feasible and less complex, but they are not reliable enough.

The direct approaches involve analyzing the brain signals captured using techniques like functional Magnetic Resonance Imaging (fMRI), functional Near Infra-Red (fNIR) etc. Currently, Electroencephalography (EEG) is extensively being used in educational tasks through the advent of Brain Computer Interface (BCI) technology. In a research, greater left temporal alpha activity was noticed when compared to that of right temporal lobe affecting the performance associated with flow. In conjunction to this, the mid beta activity and theta activity also have an effect on performance whereas there was no significant results with respect to delta waveforms. In higher alpha activity coupled with lower beta activity is found to be characterized for flow state. Recently low cost devices are being used for analyzing the effect of various elementary cognitive tasks. Some of these works also suggested using other physiological responses like GSR and heart rate for assessing the flow state. The main problem of using multichannel physiological sensors is that, the results obtained from the multiple sensors need to be fused using an appropriate mechanism.

Prior attempts at such EEG measurements, however, have not been fruitful because of two major shortcomings. First, there was the failure to measure brain activity while the subject performed a task taxing the subject's mental processes, such as working memory, that are highly related to overall performance. Merely recording brain activity while the subject sits idly, watching a meaningless flashing light, or performing a task not requiring her or his full attention is insufficient to produce patterns of brain activity characterizing changes in an individual's overall performance over an extended time period. Second, there was a reliance on single, overly simplistic measures of brain function derived from theoretical constructs without sufficient support from empirical data.

Bayesian network is becoming an increasingly popular technique to model uncertain and complex domains. Unlike classical statistical models, BN allow the introduction of prior knowledge into models. This prevents extraneous data to be considered which might alter desired results. Bayesian network uses the concept of conditional probability which is proven to be very useful in applications to the real world problem domain, where probability of occurrence of an event is conditionally dependent on the probability of occurrence of a previous event. Bayesian Network modelling has been used in the areas of medicine, document classification, information retrieval, image processing, decision support system, gaming, bioinformatics, gene analysis etc.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for detection and analysis of a learner's/performers cognitive flow. The system comprises a console, a data capture tool, an electroencephalogram (EEG) device, a GSR sensing device, a pulse oximeter, a questionnaire, a memory and a processor. The console configured to be used by the learner to perform a task at a difficulty level. The data capture tool captures a plurality of parameters related to the task. The electroencephalogram (EEG) device measures brain activity of the learner. The brain activity indicates a skill-challenge balance of the learner. The GSR sensing device for measuring galvanic skin response (GSR) of the learner. The GSR indicates the concentration of the learner. The pulse oximeter senses photo-plethysmogram (PPG) signal. The PPG signal is being used to measure heart rate variability (HRV) of the learner. The HRV indicates the stress level of the learner. The questionnaire configured to be filled by the learner after completing the task to measure the actual cognitive state of the learner. The processor coupled with the memory. The processor configured to perform the steps of: Creating a Bayesian network framework. The Bayesian network framework includes a plurality of evidence nodes, a plurality of sensor nodes and a plurality of state nodes. Next step include receiving intelligence quotient (IQ) level of the person, the plurality of parameters related to the task and the difficulty level of the task as inputs to the plurality of evidence nodes. Followed by predicting a cognitive state of the learner using the results obtained from the plurality of sensor nodes and the inputs provided at the plurality of evidence nodes. And in the final step of comparing, the predicted cognitive state with the actual cognitive state. If the predicted cognitive state is same as the actual cognitive state then the processor validates the Bayesian network framework. Else the processor resolves a conflict generated due to the difference between the predicted cognitive state and the actual cognitive state by reasoning between the nodes using probabilistic queries.

Another embodiment provides a method for the detection and analysis of learner's/performers cognitive flow. Initially, the learner is asked to perform the task. At the next step simultaneously when the learner is performing the task, various parameter of the person related to the task are recorded by a data capture tool. In the next step, the electrical signal generated by the brain is measured using the EEG device. The galvanic skin response (GSR) is measured using the GSR sensing device. And the heart rate variability (HRV) of the person is measured using the pulse oximeter. At the next step, an actual cognitive state of the learner is measured using the questionnaire. In the next step, a Bayesian network framework is created by the processor. The Bayesian network framework includes three types of nodes, i.e., a plurality of evidence nodes, a plurality of sensor nodes and a plurality of state nodes. At the next step, the IQ level of the learner, the plurality of parameters related to the task and the difficulty level of the task is provided as inputs to the processor. At the next step, the cognitive state of the learner is predicted using results obtained from sensor nodes and input provided by the evidence nodes. And finally, the predicted cognitive state is compared with the actual cognitive state by the processor. If the predicted cognitive state is same as the actual cognitive state, then it is concluded that the Bayesian network framework is validated and can be used for further analysis of the learner's cognitive state. If the predicted cognitive state is not same as the actual cognitive state, then the conflict is resolved by reasoning between the various nodes using probabilistic queries.

Another embodiment provides a non-transitory computer-readable medium having embodied thereon a computer program for executing a method for detection and analysis of a learner's cognitive flow. The method comprises asking the learner to perform a task, wherein the task is performed at a difficulty level. Further, the method comprises recording a plurality of parameters related to the task using a data capture tool. Further, the method comprises measuring brain activity of the learner by sensing an electroencephalogram (EEG) signal using an EEG device. Further, the method comprises measuring concentration of the learner by sensing galvanic skin response (GSR) using a GSR sensing device.

Further, the method comprises measuring stress level of the learner by sensing heart rate variability (HRV). Further, the method comprises measuring an actual cognitive state of the learner during the task using a questionnaire filled by the learner after performing the task. Further, the method comprises, creating, by the processor, a Bayesian network framework, wherein the Bayesian network framework includes a plurality of evidence nodes, a plurality of sensor nodes and a plurality of state nodes. Further, the method comprises providing intelligence quotient (IQ) level of the person and the difficulty level of the task as inputs to the plurality of evidence nodes. Further, the method comprises predicting, by the processor, a cognitive state of the learner using the results obtained from the plurality of sensor nodes, the inputs provided at the plurality of evidence nodes and the plurality of parameters. Furthermore, the method comprises comparing, by the processor, the predicted cognitive state with the actual cognitive state, wherein if the predicted cognitive state is same as the actual cognitive state then the processor validating the Bayesian network framework, else generating resolving a conflict generated due to the difference between the predicted cognitive state and the actual cognitive state by reasoning between the nodes using probabilistic queries.

BRIEF DESCRIPTION OF THE DRAWINGS

The embodiments herein will be better understood from the following detailed description with reference to the drawings, in which.

DETAILED DESCRIPTION OF EMBODIMENTS

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
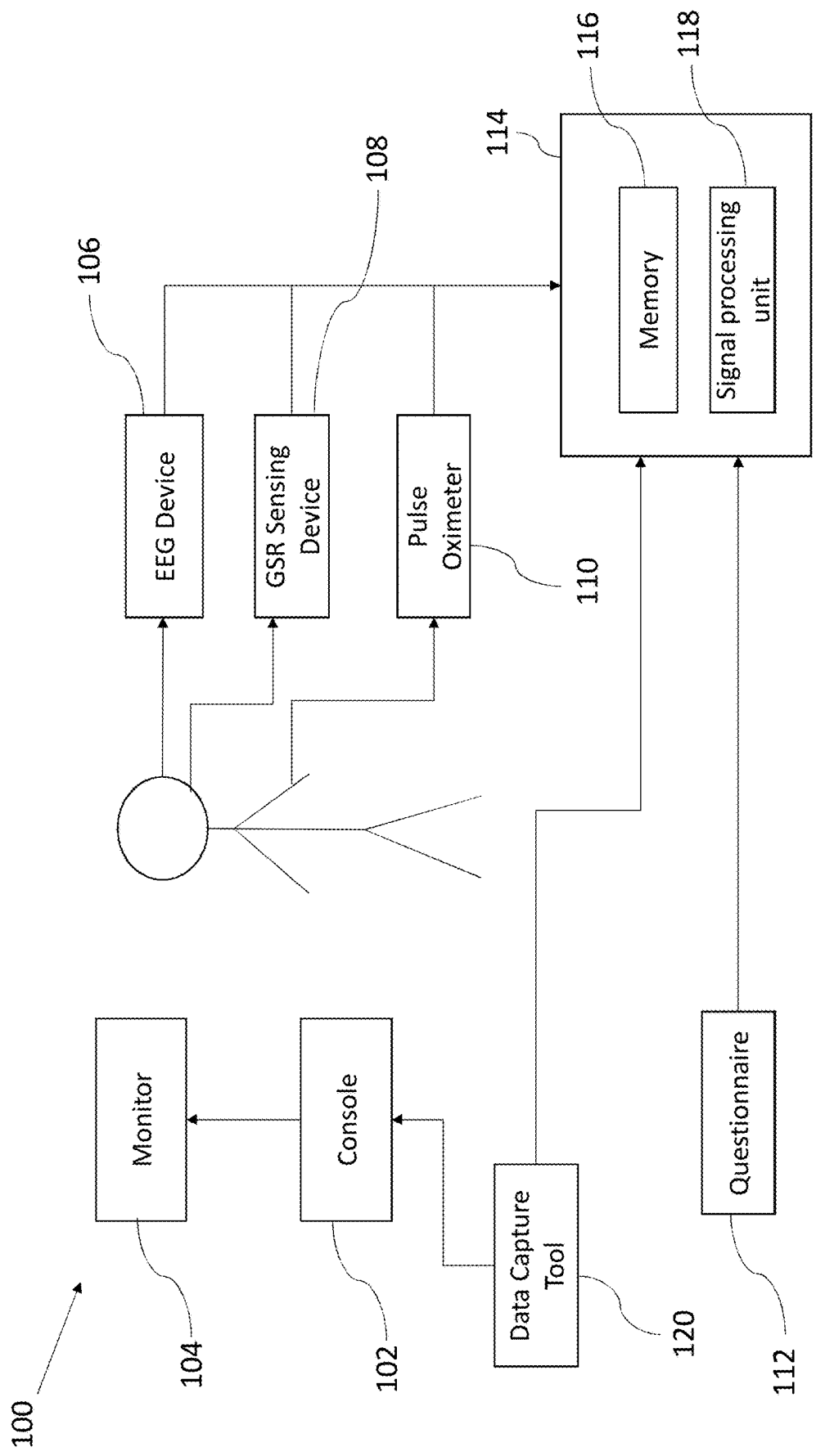
FIG. 1 shows a block diagram of a system for detection and analysis of learner's/performers cognitive flow according to an embodiment of present disclosure.

Referring now to the drawings, and more particularly to FIG. 1, where similar reference characters denote corresponding features consistently throughout the figures, there are shown preferred embodiments and these embodiments are described in the context of the following exemplary system and/or method.

Figure 4:
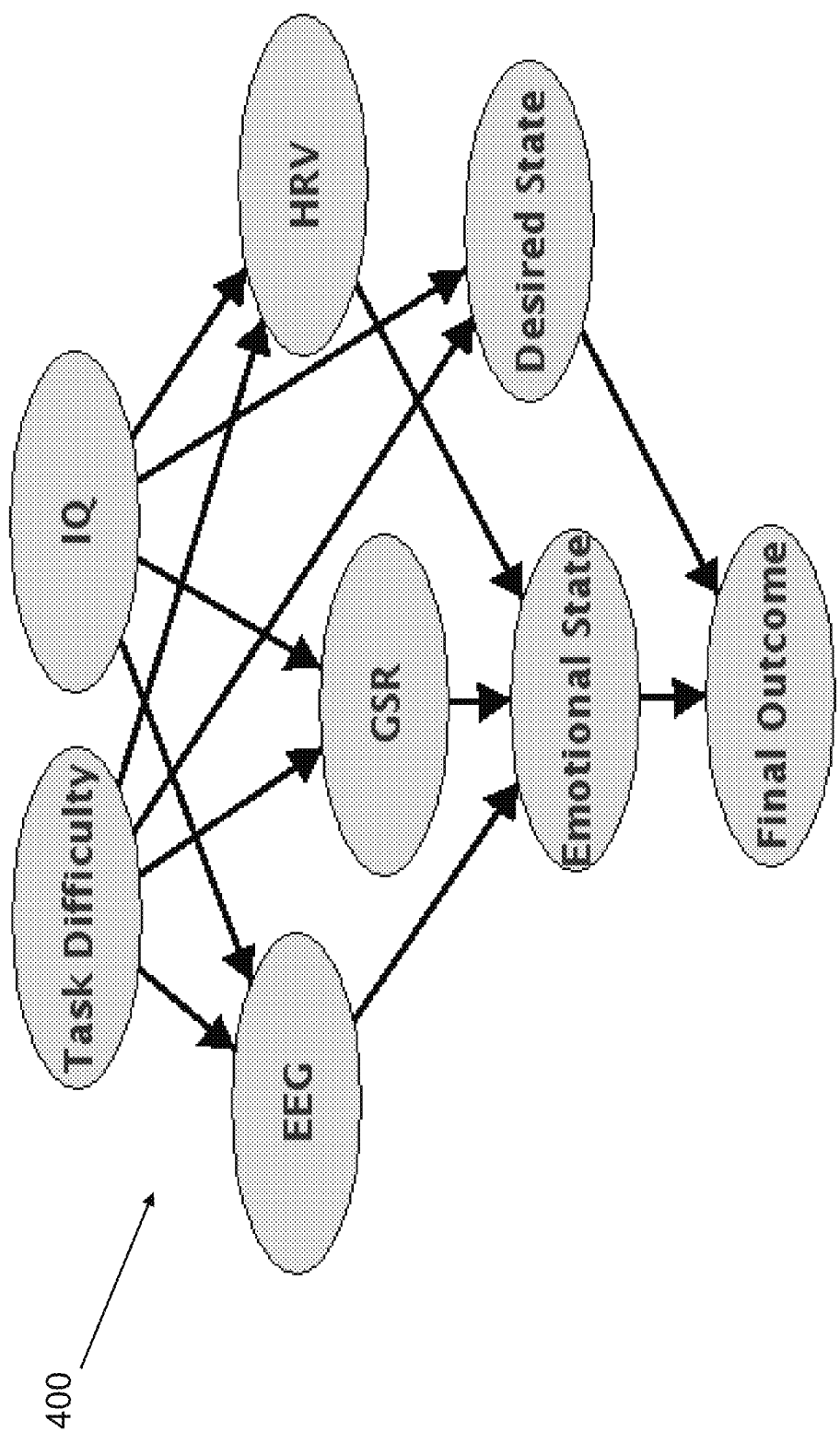
FIG. 4 shows a schematic representation of the Bayesian framework network according to an embodiment of present disclosure.

FIG. 1 illustrates a schematic block diagram of a system 100 for detection and analysis of learner's/performers cognitive flow in accordance with an embodiment of the present disclosure. The system 100 is configured to measure the cognitive state of learner/performer, while they are performing tasks of various complexity levels, using physiological responses like brain activation, heart rate variability and galvanic skin response. It should be appreciated that the words 'learner', 'person', 'participant', and 'performer' will be used interchangeably in the present disclosure. The system 100 uses a Bayesian network based framework 400 to probabilistically evaluate the cognitive state of the learner from the difficulty levels of the tasks, IQ level of the learner and observations made using the physiological sensing as shown in FIG. 4.

Figure 2:
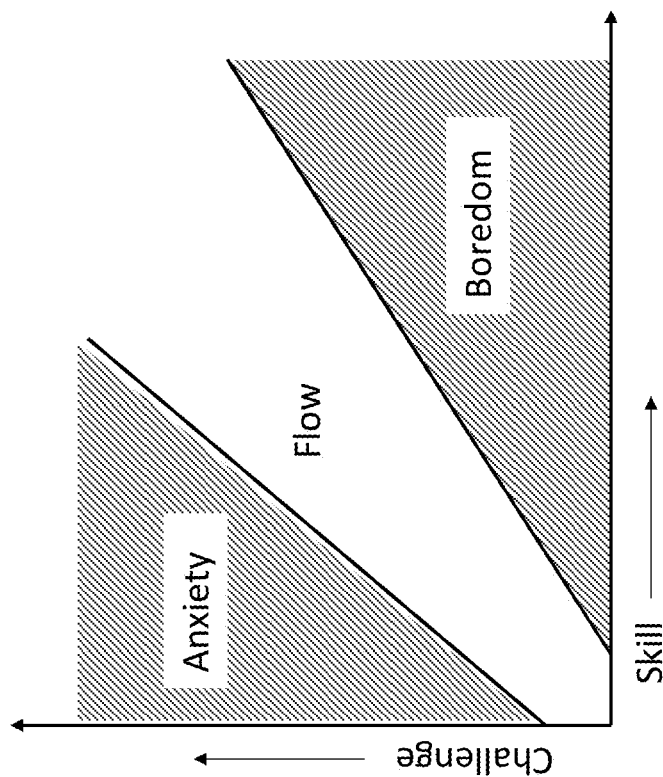
FIG. 2 shows a graphical representation of the flow state, anxiety and boredom state according to an embodiment of present disclosure.

The flow state of the learner is directly associated with the mental state of the learner. The flow state can determine whether the learner is in anxiety state or boredom state as shown in the graph 300 of FIG. 2. When skill is too low and the task too challenging, the learner becomes anxious. Alternatively, if the task is too easy and skill is comparatively higher, the learner becomes bored. However, when skill and challenge are roughly proportional, people enter flow state i.e. a state of focused concentration and enjoyment.

The system 100 includes a console 102, a monitor 104, an electroencephalogram (EEG) device 106, a galvanic skin response (GSR) sensing device 108, a pulse oximeter 110, a questionnaire 112, and a processor 114. The processor 114 further includes a memory 116, which is configured to store the data generated by various components of the system 100. The system 100 also includes a signal processing unit 118 to pre-process the EEG signal captured by the EEG device 106.

According to an embodiment of the disclosure, the learner is asked to perform an activity or a task. The task is performed by the learner using the console 102. Generally a game can be used as the task which is performed by the learner. In an embodiment of the disclosure, a Tower of London (TOL) game is used as the task. Though it should be appreciated that the use of any other game is well within the scope of this disclosure.

Figure 3:
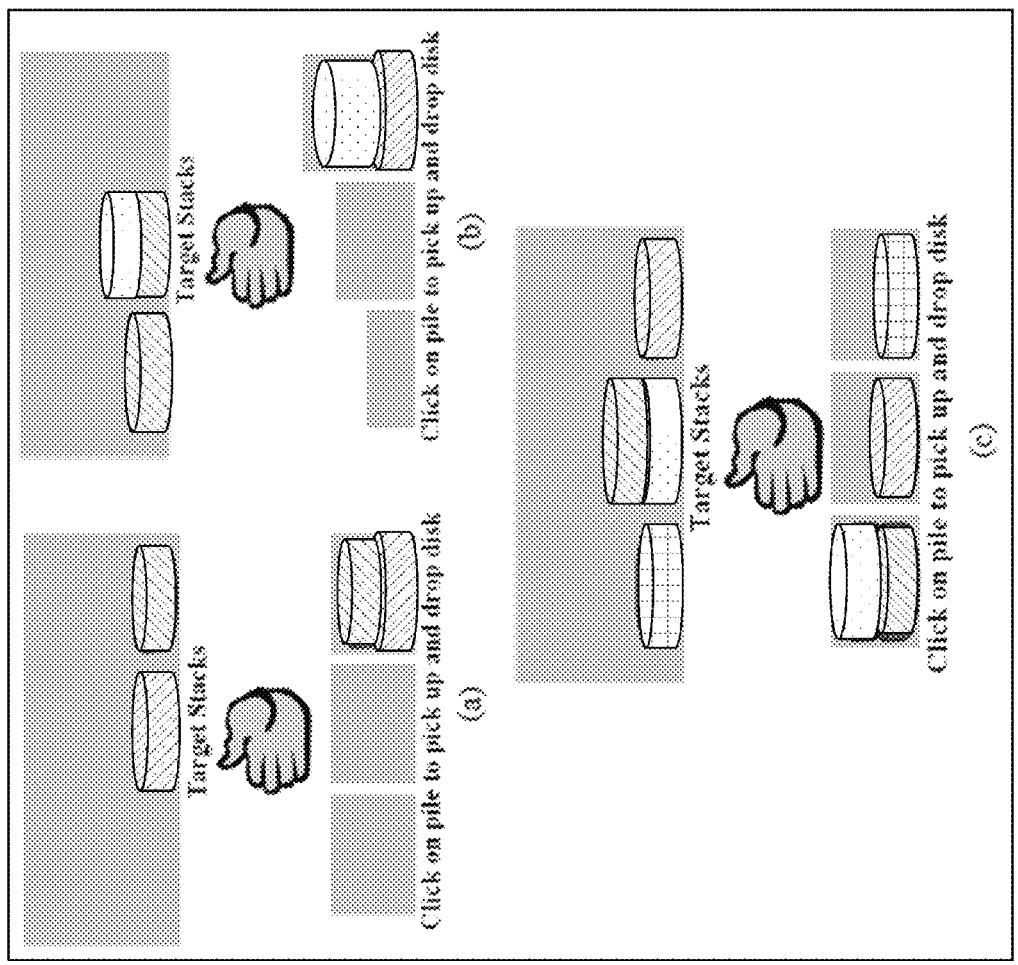
FIG. 3 shows a screenshot of Tower of London games in three level of difficulties according to an embodiment of present disclosure.

The Tower of London (TOL) is a classical puzzle based game used by psychologists for assessment of executive functions and planning capabilities of an individual. The standard TOL game was modified for three levels of difficulties (Difficult, Moderate and Easy) in PEBL. For a game session, a target configuration is shown at the top of the screen as shown in FIG. 3. The goal is to move a pile of disks given at the bottom so that the given assembly matches the target configuration shown on the top of the screen. Participants can only move one disk at a time, and cannot move a disk onto a pile that has no more room (indicated by the size of the grey rectangle). Participant has to click on the pile they want to move a disk off, and it will move up above the piles. Next, they click on another pile, and the disk will move down to that pile. There is a time limit to finish each game. Participants are instructed to finish each game within the allotted time. If the participant fails to finish the game within the session related time, the session ends and a new game starts. Various parameters related to the learner were recorded. The various parameters include information like start time of the game, duration, number of moves, total number of success etc. per session.

The complexity of each game is determined with the help of the number of different colored disks, the minimum number of moves needed to finish the game and the number of available empty space among the stacks for the disk to move around. Hence, the game complexity $G_{com}$ is defined as, $$G_{com} = \frac{N}{N_{disk} + N_{space}} \qquad (1)$$

where, N is the total number of moves, $N_{disk}$ is number of disks in the game and $N_{space}$ and is the available number of empty space.

Screen shots for three different levels of games are shown in FIG. 3. The minimum number of moves per disk for the low difficulty game is chosen as two and the total number of different disk is two, the complexity for this level of game is $3/(2+4)=0.5$. Similarly, the complexities for the medium difficulty game is $4/(3+3)=0.67$ and high difficulty game is $8/(4+2)=1.33$ according to equation (1). These calculations show that the complexity for each task increases with respect to increase in difficulty level.

According to an embodiment of the invention, the system 100 is configured to measure the physiological signal of the learner while playing the game. In an embodiment, an in house python based tool is used for the data collection. The tool simultaneously captures the EEG, GSR and Photoplethysmogram (PPG) signals of the learner. The EEG signal is measured by sensing the direct electrical activities from the brain using the EEG device 106. In an example of the invention, Neurosky EEG device has been used to capture the electrical activities of the brain. The learner is asked to play the game while wearing a single lead EEG device from Neurosky. It is a dry sensor with a lead placed in FP1 position and the grounding is done with reference to left earlobe.

According to an embodiment of the disclosure, the captured EEG signal is further analyzed using the signal processing unit 118. Various frequency band energies and time domain Hjorth parameters were experimented as shown in equation (2) and (3)

$$F = \{E^{\delta}, E^{\theta}, E^{\alpha}, E^{l\beta}, E^{m\beta}, H^{a}, H^{m}, H^{c}\} \qquad (2)$$

The first five features are the energies in various frequency bands namely, delta ($E^{\delta}$ as 0.5-4 Hz), theta ($E^{\theta}$ as 4-7.5 Hz), alpha ($E^{\alpha}$ as 7.5-12.5 Hz), low-beta ($E^{l\beta}$ as 12.5-16 Hz) and mid-beta ($E^{m\beta}$ as 16-20 Hz) respectively. The energies in each band are extracted using Welch's power spectral density. The last three features in equation (2) are the Hjorth parameters namely Activity ($H^a$), Mobility ($H^m$) and Complexity ($H^c$) respectively as given in equation (3)

$$H^a = \text{var}(x(t)) \quad H^m = \sqrt{\frac{H^a\left(\frac{dx(t)}{dt}\right)}{H^a(x(t))}} \quad H^c = \frac{H^m\left(\frac{dx(t)}{dt}\right)}{H^m(x(t))} \quad (3)$$

Here x(t) indicates the time domain signal in a window of duration 1 sec and $$\frac{dx(t)}{dt}$$

is the first order derivative of the signal.

According to an embodiment of the invention, the galvanic skin response of the person is measured using the galvanic skin response (GSR) sensing device 108. In an example, the GSR sensing device 108 from eSense is used to record the variations in skin conductance level. The GSR is an electro-dermal response where the skin conductance changes with the state of the sweat glands in presence of stressful, likeable events. Therefore GSR is be a good predictor of concentration, mental workload etc. in flow study. The GSR sensing device 108 applies a constant voltage to the skin of the person through two electrodes. The voltage is so small that it cannot be felt or perceived by the individual. However, the current that flows through the skin, as the voltage is applied, can be detected. The GSR signal is characterized by two components: a fast component called 'phasic' and a slow component called 'tonic'. Both tonic and phasic components contain information associated with specific physiological aspects of brain states. Here the tonic component is calculated only by taking the inverse transform of first few Fourier coefficients as given in equation (4), whereas the phasic component is calculated by inversing the higher coefficient of Fourier coefficients as given in equation (5).

$$T_c = IFFT\left(\sum_{n=0}^{N-1} x(n) \cdot e^{-j\left(\frac{2\pi}{N}\right)nk}\right), k = 0, 1, 2, 3 \quad (4)$$

$$P_c = IFFT\left(\sum_{n=0}^{N-1} x(n) \cdot e^{-j\left(\frac{2\pi}{N}\right)nk}\right), k = 4, 5, \ldots N-1 \quad (5)$$

$$T_c^{mean} = \text{mean}(T_c(n)), T_c^{kurt} = kurtosis(T_c(n)), 1 \leq n \leq N \quad (6)$$

According to an embodiment of the invention, the stress level of the learner is measured using the heart rate variability (HRV) of the person. When the challenge of the undertaking activity is low compared to the person's skill level, then the heart rate variability (HRV) is high compared to the flow state where the skill matches with the challenge level required. The HRV of the person can be measured using the pulse oximeter 110 wearable on the index finger for sensing the Photoplethysmogram (PPG) signal. The oxygen saturation level and the pulse rate are measured by the pulse oximeter from Contec, through the left ring finger. In an embodiment of the invention, the HRV is calculated in three time domain HRV parameters namely 1) rMSSD (Root mean square of successive differences between adjacent NN intervals), 2) SDSD (Standard deviation of successive differences between adjacent NN intervals), 3) SDNN (Successive difference between NN Intervals).

According to an embodiment of the invention, the system uses a questionnaire 112 to get the feedback of the learner. In an example a standard Game-flow indicator (GFI) feedback form has been used to assess if the learner experienced boredom and flow experiences during the game and the findings are used as the reference. This questionnaire based feedback form is ideal to measure level of engagement while playing a game. For doing this, the overall scores for both flow and boredom questionnaires are calculated assuming 1=strongly disagree, 2=disagree, 3=undecided, 4=agree and 5=strongly agree. Different questions are asked regarding the experience of participants while playing the game. The participants are asked to fill up three feedback forms, one for each of the three games, immediately after the end of each session. This feedback provide an actual cognitive state along with the game data.

According to an embodiment of the disclosure, the system 100 creates a Bayesian network framework 400 as shown in FIG. 4. The Bayesian network consists of three types of nodes i.e. a plurality of evidence nodes, a plurality of sensor nodes and a plurality of state nodes. The plurality of evidence nodes include Task Difficulty (TD), Intelligence Quotient (IQ). The plurality of sensor nodes include GSR, EEG and HRV. The plurality of state nodes include emotional State (O), desired State (D), and final Outcome (F) state. Various nodes are connected to few other nodes as shown in FIG. 4.

The Bayesian Network (BN) framework is created with the objective to diagnose and investigate the different relationships between the sensors nodes and the state nodes. Through the Evidence nodes the static knowledge or evidence is provided as input. In an embodiment of the disclosure, the IQ level of the learner and also the difficulty levels of task/game they are given. The Evidence nodes serve as parents to the Sensor nodes, since the sensor readings are a direct causal effect of the two conditions (IQ & TD). Based on the results obtained from physiological sensors, the current cognitive state of the learner is predicted.

The Bayesian Network framework 400 is created in Samlam, a comprehensive tool for modelling and reasoning with Bayesian networks, developed in Java by the Automated Reasoning Group of Professor Adnan Darwiche, UCLA. The IQ level and the task difficulty (TD) level serve as evidence nodes in the BN. Depending on the state of these two nodes, the physiological sensor readings vary. Hence all the sensor nodes have them as immediate parents.

According to an embodiment of the disclosure, the system 100 is further configured to compare the actual cognitive state with the current cognitive state. The readings of all three sensors i.e. the EEG device 106, the GSR sensing device 108, the pulse oximeter 110, are used to analyse the cognitive state of the learner and are compared to the ground truth i.e. the actual cognitive state. If two state matches, then it can be concluded that the predicted cognitive state via the Bayesian Network is expected to give the correct outcome. If not, then there is a case of contradiction caused by one of more sensors giving faulty state. In case of a contradiction between predictive cognitive state and predicted cognitive state, the BN model can be used to resolve this conflict by reasoning between the various nodes using probabilistic queries.

Figure 5A:
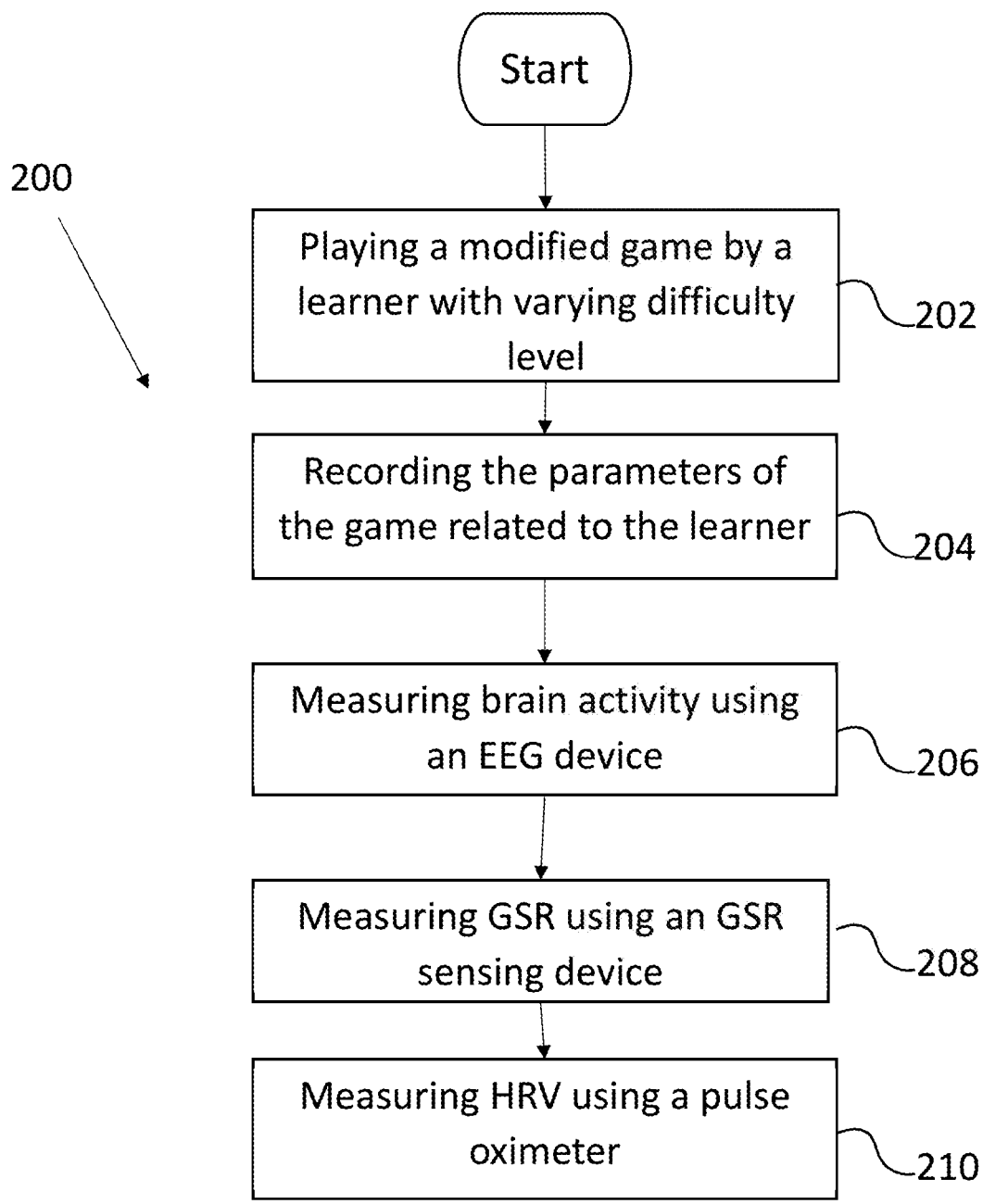
FIG. 5A,5B,5C shows a flow chart illustrating steps involved in detection and analysis of learner's/performers cognitive flow according to an embodiment of present disclosure.
Figure 5B:
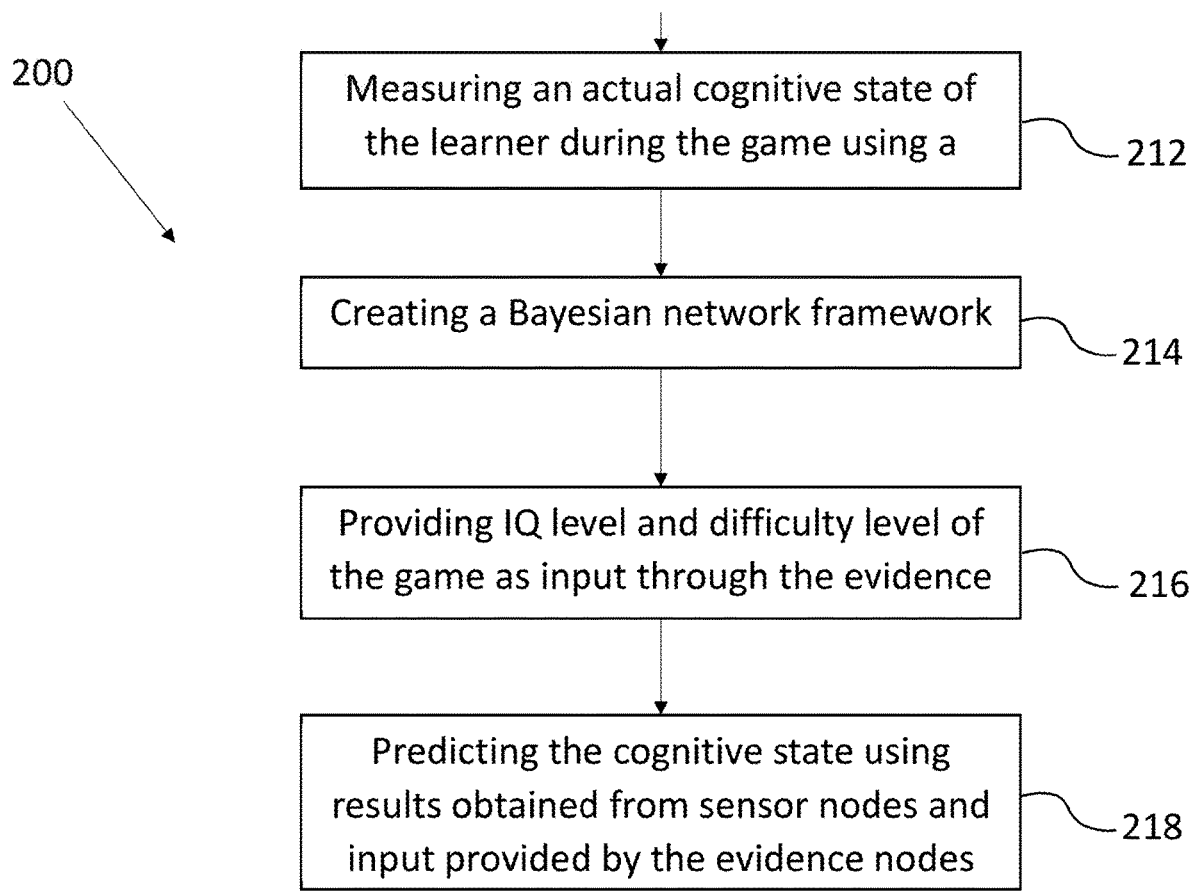

In operation, a flowchart 200 illustrating the steps involved for the detection and analysis of learner's cognitive flow in accordance with an embodiment of the present disclosure is shown in FIG. 5A. Initially at step 202, the person is asked to perform a task. In an embodiment the learner is asked to play a game such as Tower of London with varying difficulty levels. At the next step 204, simultaneously when the learner is performing the task, various parameter of the person related to the game are recorded by a data capture tool 120. At step 206, the electrical signal generated by the brain is measured using the EEG device 106. EEG signal measures the skill-challenge balance of the person. In an example, a standard Neurosky device has been used for the measuring. The EEG device 106 captures mid-beta and theta frequency of the EEG signal for the analysis. In the next step 208, the galvanic skin response (GSR) is measured using the GSR sensing device 108. In the next step 210, heart rate variability (HRV) of the person is measured using the pulse oximeter 110. It should be appreciated that the step 206, 208 and 210 are being performed simultaneously when the person is performing the activity. At the next step 212 in FIG. 5B, an actual cognitive state of the learner is measured using the questionnaire 112. The learner is asked to fill up the questionnaire after finishing the task. The questionnaire 112 is used to obtain an indication of person's perception during flow and boredom experience.

In the next step 214, a Bayesian network framework is created by the processor 114. The Bayesian network framework 400 includes three types of nodes, i.e., a plurality of evidence nodes, a plurality of sensor nodes and a plurality of state nodes. The plurality of evidence nodes includes Task Difficulty (TD), Intelligence Quotient (IQ) of the learner. The plurality of sensor nodes include the physiological sensors output i.e. EEG, GSR and HRV. The plurality of state nodes include Emotional State (O), Predicted State (D) and Final Outcome (F). At the next step 216, the IQ level of the learner and the difficulty level of the game is provided as an input to the processor 114. In an embodiment the difficulty level could one of a high low or medium as mentioned previously. At step 218, the cognitive state of the learner is predicted using results obtained from sensor nodes and input provided by the evidence nodes.

Figure 5C:
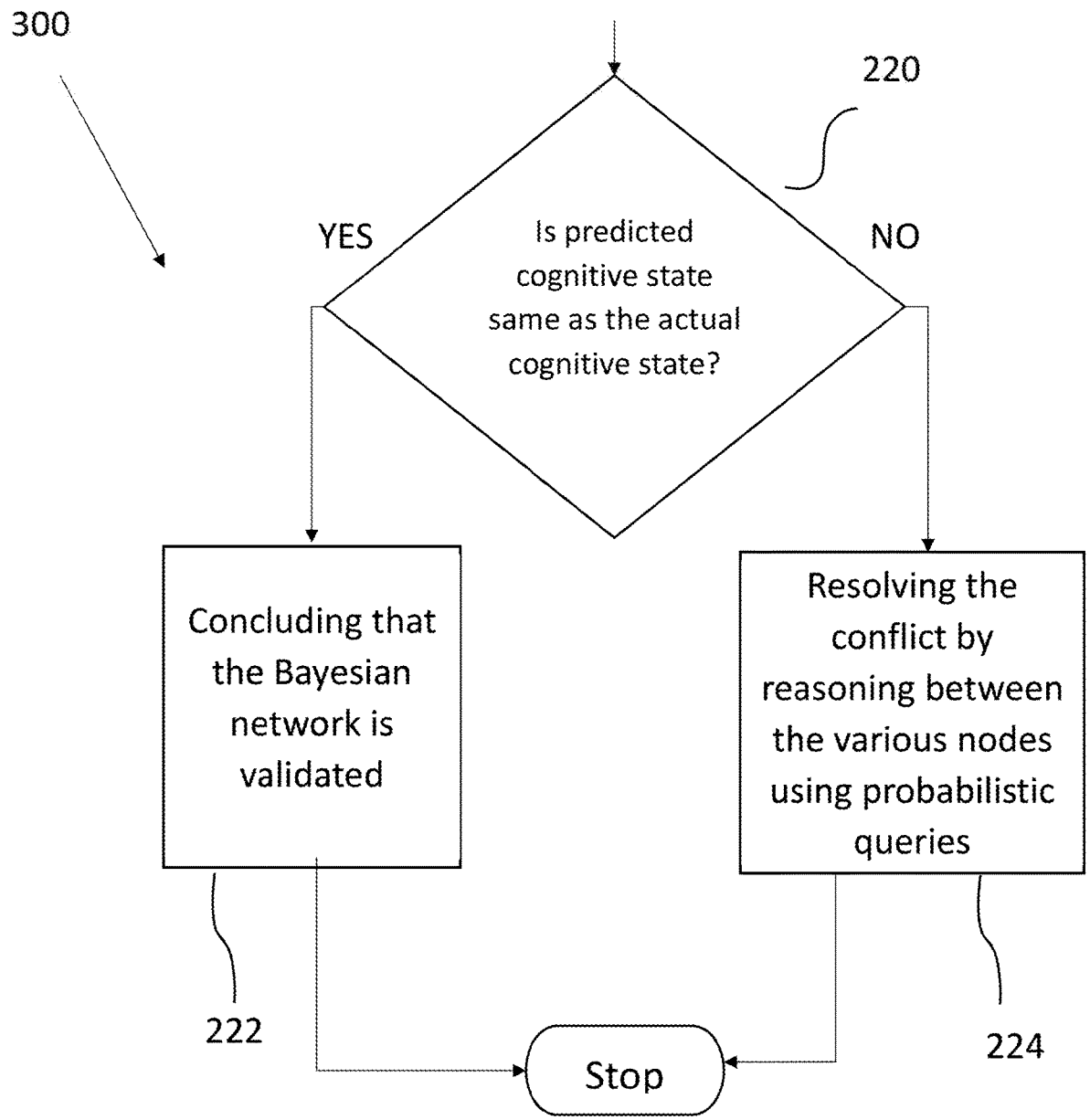

At step 220 in FIG. 5C, the predicted cognitive state is compared with the actual cognitive state by the processor 114. If the predicted cognitive state is same as the actual cognitive state, then at step 222, it is concluded that the Bayesian network framework is validated and can be used for further analysis of the learner's cognitive state. If the predicted cognitive state is not same as the actual cognitive state, then at step 224, the conflict is resolved by reasoning between the various nodes using probabilistic queries.

It should be appreciated that the system 100 can be used to distinguish the performance for the participants in three different level tasks. The system 100 can be fused together and analyzed along with the performance and feedback data to get further insights of the mental state for the participant.

From our proposed Bayesian Network it was determined whether there is a contradiction between observed and desired state. In case of contradiction, it was found out whether there are any sensor(s) nodes giving faulty data. Moreover, the workflow of the Bayesian Network should be dynamic for handling a large number of data. Several knowledge under uncertainty can be determined in future by using such probabilistic graphical models. In the area of education, models can be designed for generating a sequence of questions which are intermixed in difficulty level to analyze the variation in cognitive states of an individual during the assessment process A working example of the present invention is explained as follows according to an embodiment of the disclosure:

A group of 20 people were randomly selected to perform the experiments. The IQ scores are found to vary between 80 and 131. The average age of the participants are 22-30 years. They are all right handed male engineers belonging to similar socio-economic background. They had normal or corrected to normal vision. The selection is made to reduce the participant related bias so that the variation is only in their IQ levels.

Each of the people are asked to play the modified Tower of London game as mentioned above. Each of the participants were asked to play the game in three difficulty levels i.e. High, Low and Medium. The low difficulty level session consist of 10 set of games with 30 sec duration each. Similarly the medium session consist of 6 set of games each having 30 sec duration. The difficult session consist of 4 set of games with 30 sec duration each. For lower complexity game it is usually finished by most of the participants before 30 seconds, hence the number of games for various complexity levels are varied so that the completion time for easy, medium and hard sessions are comparable. Finally, it is found that for all the participants the minimum time to complete among all types (low, medium and high) of tasks is 90 seconds, hence the corresponding sensor data are considered for further processing.

The physiological data from the person is then collected using an in-house python based tool. The application enables us to show the stimulus in a standard computer screen and at the same time collect the EEG signals. Subjects are asked to play the game while wearing a single lead EEG device from Neurosky. It is a dry sensor with a lead placed in FP1 position and the grounding is done with reference to left earlobe. For recording the variance in skin conductance level, a GSR device from eSense was used. All the participants are right handed and hence the GSR sensors was put on the middle and ring fingers of the left hand. The right hand is kept completely free so that the user can play the game comfortably. The oxygen saturation level and the pulse rate are assessed by the pulse oximeter from Contec (CMS50DL1), through the left index finger.

After performing the above activities, the results were obtained. The feedback of the person was taken using the questionnaire based survey using GFI. The overall scores for both flow and boredom questionnaires are calculated assuming 1=strongly disagree, 2=disagree, 3=undecided, 4=agree and 5=strongly agree. The questionnaire helped in the measurement of the actual cognitive state of the participant's mind.

Figure 6:
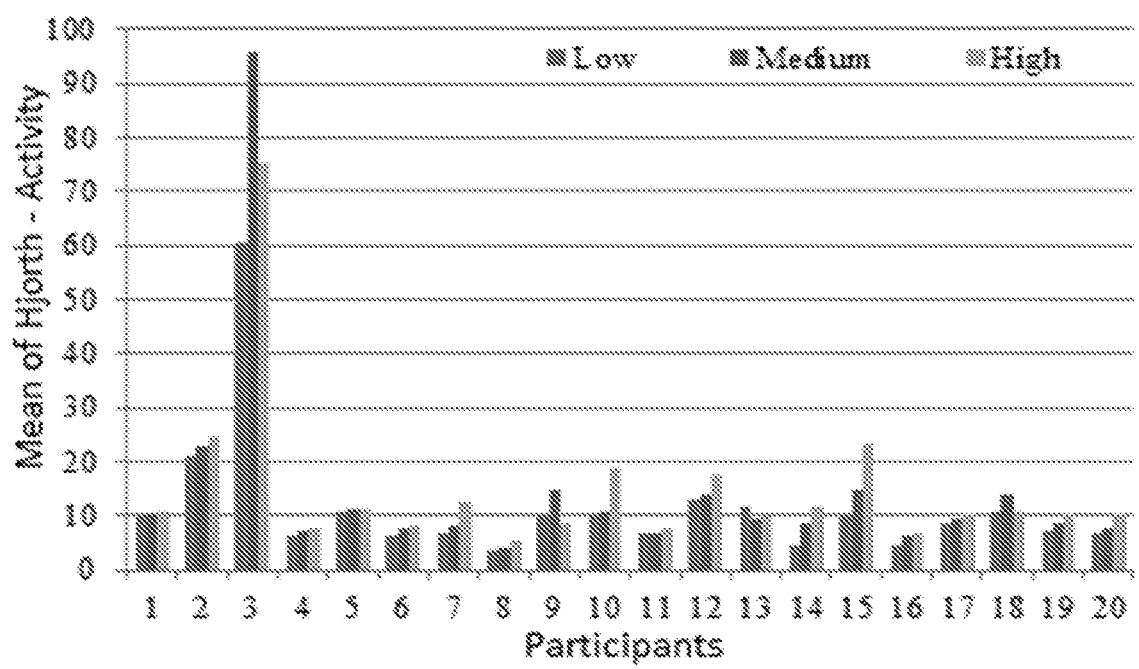
FIG. 6 is graphical representation of separation between Low, Medium, High difficulty task for the Hjorth calculation of EEG signals for 20 subjects according to an embodiment of present disclosure.
Figure 7:
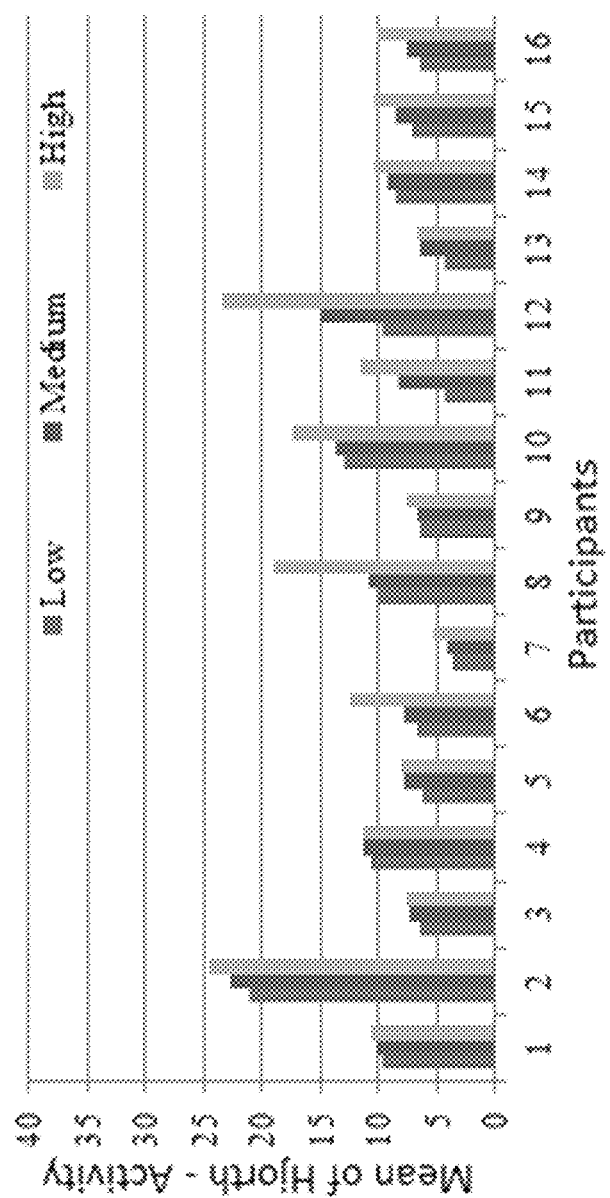
FIG. 7 is graphical representation of separation between Low, Medium, High difficulty task for the Hjorth calculation of EEG signals for 16 subjects according to an embodiment of present disclosure.

Various features of the EEG signals namely alpha, beta, theta, delta, attention, meditation, Hjorth etc. for all the experiments for all the participants are extracted using equation (2) and (3). Among all features the Activity measure of Hjorth parameter is found to be indicative of variations of brain signals with difficulty level. The raw EEG signal is used for calculating activity for windows of duration 1 sec and the overall mean is taken for each session of the game of all the participants. The results for different difficulty levels (Low, Medium and High) are combined separately for all the 20 participants and compared as shown in FIG. 6. It was found that good amount of separation between three different tasks for 16 out of 20 participants. The comparison for these selected participants are shown in FIG. 7.

Figure 8:
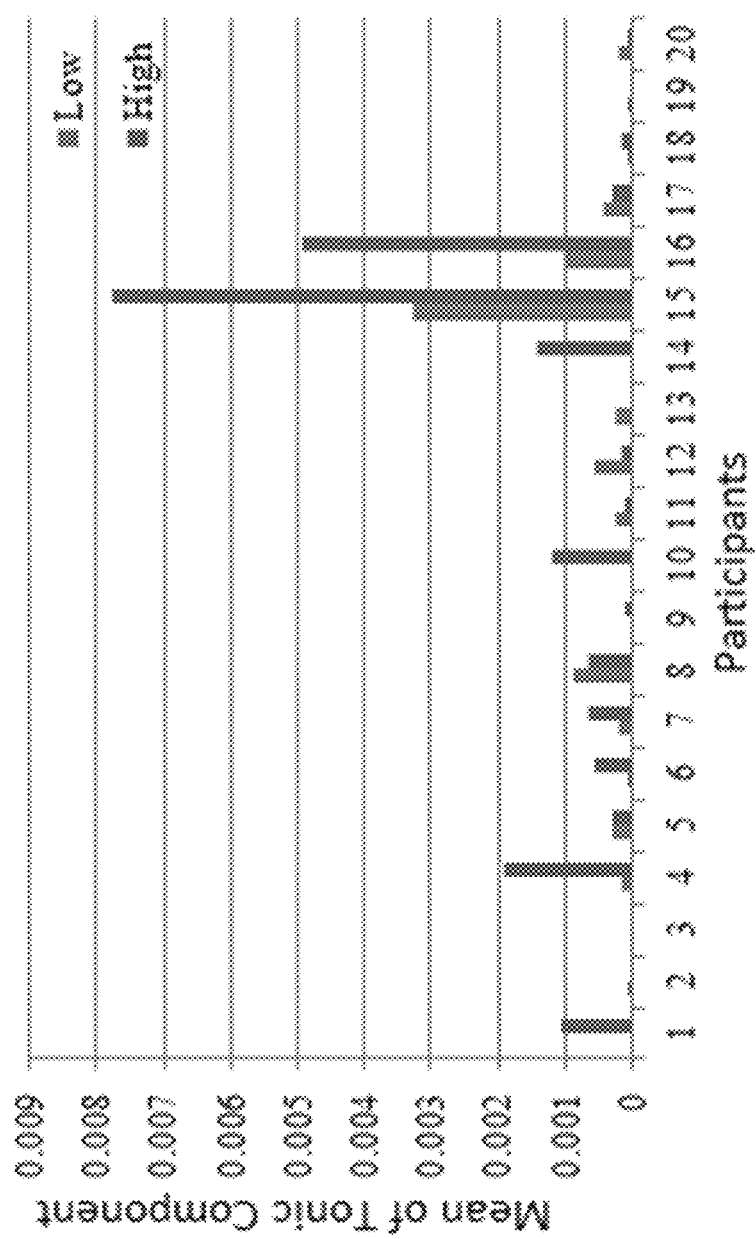
FIG. 8 is graphical representation of separation between the Mean of the Tonic (μS) component of GSR during the Low and High difficulty according to an embodiment of present disclosure.
Figure 9:
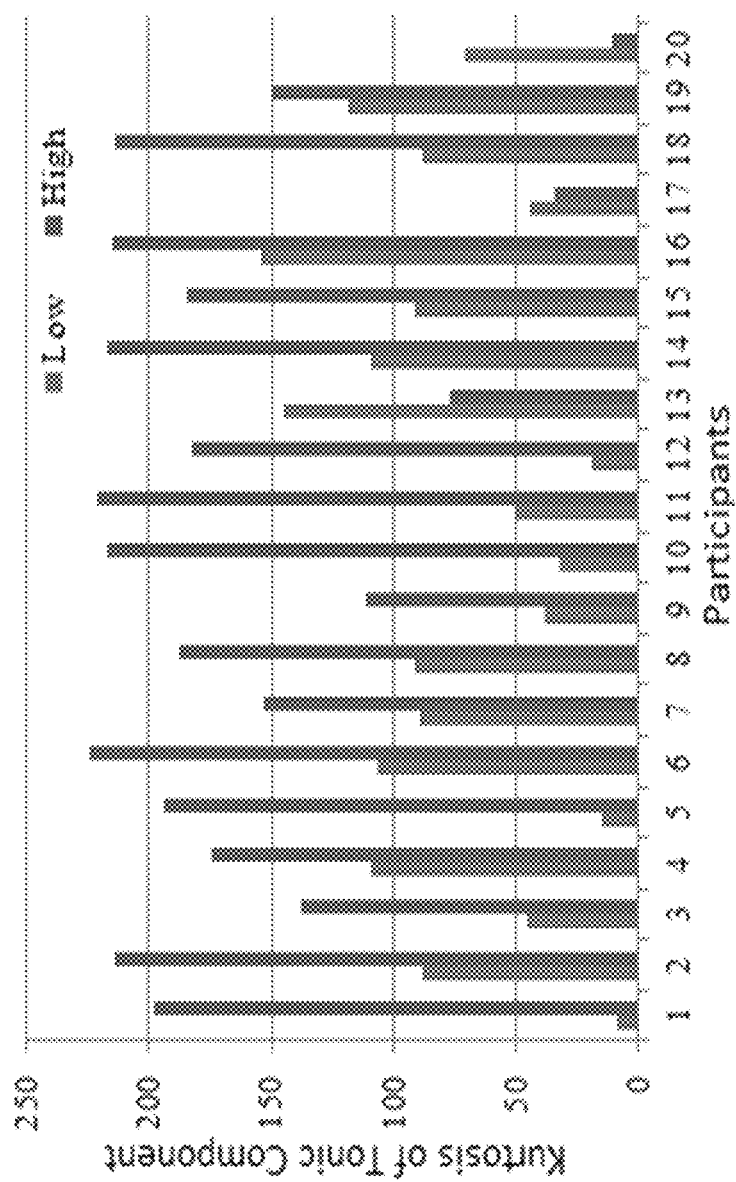
FIG. 9 is graphical representation of separation between the Kurtosis of the Tonic (μS) component of GSR during the Low and High difficulty games according to an embodiment of present disclosure.

The GSR data is subdivided into a number of windows of duration 1 sec. Next both tonic and phasic power was calculated using equation (4) and (5). The phasic power does not show sufficient separation between different task levels whereas the tonic gives good separation. The mean and kurtosis of the tonic power is calculated using equation (6). The plot of mean and kurtosis of tonic component for GSR are shown in FIG. 8 and FIG. 9. The line representing the medium difficulty game for all the subjects is found to overlap over the other two. The separation between the medium games across participants is not consistent. Hence for better representation, only the GSR for high and low difficulty games were plotted.

Figure 10:
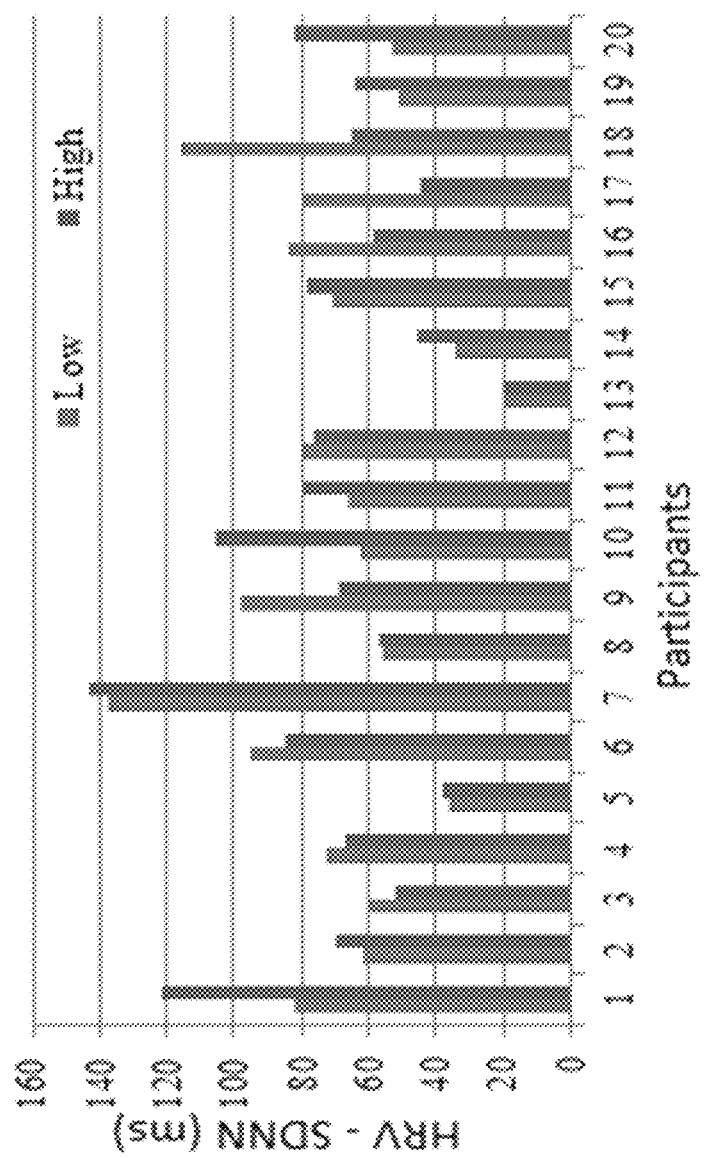
FIG. 10 is graphical representation of separation of the HRV (SDNN) in msec for all the 20 subjects between the high and low difficulty game according to an embodiment of present disclosure.

The PPG signal analysis does not give a clear, consistent separation between difficulty levels of the task for all the participants. The successive difference between NN intervals (SDNN) were plotted in FIG. 10. For 10 out of 20 subjects there is a separation between the two SDNN values out of which only 5 have the value for the low game lower than the high game. Hence any substantial information cannot be derived from this result of PPG analysis.

The Bayesian network framework, given in FIG. 4, has been trained based on the results obtained from physiological sensor data collected during the experiments. The conditional probability tables associated with each node have been updated according to the occurrence of their respective parent node. Given a participant of a particular IQ level and solving a game of a particular difficulty level, each of the sensor data was collected and their probability of occurrence was calculated over all possible conditions. The scores of IQ less than 89 are treated as Low IQ, scores between 90 and 109 are treated as Medium IQ and scores with 110 is treated as High IQ. In the present study 6 participants having high IQ, 9 participants having medium IQ and 5 participants having low IQ.

The data for 18 out of 20 participants was used to train the BN. The sensor data for all the training participants (18 subjects) are classified into three levels (Low, Medium, High) based on their observations. An example is shown in Table 1 below where the levels of the EEG sensor data are shown for 5 training participants with High IQ, playing three levels of games. It can be seen that for the easy game (TD=low), all of them have low EEG feature values, for medium game (TD=medium), one of them has high EEG feature and similarly for difficult game (TD=high). The probability of occurrence of each level is calculated and updated in the respective Conditional Probability Table (CPT) of the BN. After the training the final CPT for the EEG node is shown in Table 2. The same rule is followed for the rest of the sensor nodes as well.

TABLE 1

| TD | | | EEG level (Mean of Hjorth-Activity) | | |
|---|---|---|---|---|---|
| L | L | L | L | L | L |
| M | M | H | M | M | M |
| H | H | M | H | H | H |

TABLE 2

| EEG | (L, H) | (M, H) | (H, H) | (L, M) | (M, M) | (H, M) |
|---|---|---|---|---|---|---|
| L | 0.98 | 0.02 | 0.02 | 0.98 | 0.01 | 0.01 |
| M | 0.01 | 0.79 | 0.19 | 0.01 | 0.98 | 0.01 |
| H | 0.01 | 0.19 | 0.79 | 0.01 | 0.01 | 0.98 |

TABLE 2-continued

| EEG | (L, L) | (M, L) | (H, L) |
|---|---|---|---|
| L | 0.5 | 0.25 | 0.25 |
| M | 0.25 | 0.5 | 0.25 |
| H | 0.25 | 0.25 | 0.5 |

The data for the remaining 2 participants (having high IQ and low IQ) are used to validate whether the BN nodes are providing the correct results. Different combinations of evidences for these two subjects are checked in the BN and the reasons for contradictions are explained. The states of the BN are shown as rectangular blocks containing the percentage equivalent of the probability values of the random variables.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of measuring customer experience. The embodiment, thus provides the system and method for measuring the customer experience across the plurality of business channels in the organization.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

We claim:

1. A method for detection and analysis of a learner's cognitive flow, the method comprising:
    asking the learner to perform a task, wherein the task is performed at a difficulty level;
    recording EEG, GSR and HRV parameters related to the task using a data capture tool;
    measuring brain activity of the learner by sensing an electroencephalogram (EEG) signal using an EEG device;
    measuring galvanic skin response (GSR) of the learner using a GSR sensing device;
    measuring stress level of the learner by sensing heart rate variability (HRV);
    measuring an actual cognitive state of the learner after the task using a questionnaire filled by the learner after performing the task;
    creating, by a processor, a Bayesian network framework, wherein the Bayesian network framework includes a plurality of evidence nodes, a plurality of sensor nodes and a plurality of state nodes and wherein the plurality of sensor nodes include the EEG, GSR and HRV parameters;
    providing intelligence quotient (IQ) level of the learner and the difficulty level of the task as inputs to the plurality of evidence nodes;
    predicting, by the processor, a cognitive state of the learner using results obtained from the plurality of sensor nodes and the inputs provided at the plurality of evidence nodes;
    comparing, by the processor, the predicted cognitive state with the actual cognitive state,
        wherein if the predicted cognitive state is same as the actual cognitive state then the processor validates the Bayesian network framework, else
        the processor resolves a conflict generated due to a difference between the predicted cognitive state and the actual cognitive state by reasoning between the nodes using probabilistic queries.

2. The method of claim 1, wherein the difficulty level is at least one of a high, medium and low level.

3. The method of claim 1 wherein the HRV is measured by sensing a photo-plethysmogram (PPG) signal using a pulse oximeter.

4. The method of claim 1, wherein the task include playing a modified Tower of London game on a console.

5. The method of claim 4, wherein the difficulty level of the modified Tower of London game is dependent on number of moves made by the learner, total number of disks and amount of empty space available.

6. The method of claim 1 further include analyzing mid-beta and theta frequency of the EEG signal of the learner.

7. The method of claim 1, wherein the questionnaire includes a set of questions related to flow and boredom states in the task.

8. A system for detection and analysis of a learner's cognitive flow, the system comprising:
    a console configured to be used by the learner to perform a task at a difficulty level;
    a data capture tool to capture EEG, GSR and HRV a plurality of parameters related to the task;
    an electroencephalogram (EEG) device for measuring brain activity of the learner, wherein the brain activity indicates a skill-challenge balance of the learner;
    a GSR sensing device for measuring galvanic skin response (GSR) of the learner, wherein the GSR indicates a concentration of the learner;
    a pulse oximeter for sensing a photo-plethysmogram (PPG) signal, the PPG signal being used to measure heart rate variability (HRV) of the learner, wherein the HRV indicates a stress level of the learner;
    a questionnaire configured to be filled by the learner after completing the task, to measure an actual cognitive state of the learner;
    a memory; and
    a processor coupled with the memory, wherein the processor is configured to perform steps of:
        creating a Bayesian network framework, wherein the Bayesian network framework includes a plurality of evidence nodes, a plurality of sensor nodes and a plurality of state nodes wherein the plurality of sensor nodes include the EEG, GSR and HRV parameters;

receiving intelligence quotient (IQ) level of the learner, and the difficulty level of the task as inputs to the plurality of evidence nodes;

predicting, by the processor, a cognitive state of the learner using the results obtained from the plurality of sensor nodes and the inputs provided at the plurality of evidence nodes;

comparing, by the processor, the predicted cognitive state with the actual cognitive state,
wherein if the predicted cognitive state is same as the actual cognitive state then the processor validates the Bayesian network framework, else
the processor resolves a conflict generated due to a difference between the predicted cognitive state and the actual cognitive state by reasoning between the nodes using probabilistic queries.

9. The system of claim 8, wherein the difficulty level is at least one of a high, medium and low level.

10. The system of claim 8, wherein the plurality of state nodes include emotional state, desired state and final outcome state.

11. A non-transitory computer-readable medium having embodied thereon a computer program method for detection and analysis of a learner's cognitive flow, the method comprising:

asking the learner to perform a task, wherein the task is performed at a difficulty level;

recording EEG, GSR and HRV parameters related to the task using a data capture tool;

measuring brain activity of the learner by sensing an electroencephalogram (EEG) signal using an EEG device;

measuring galvanic skin response (GSR) of the learner using a GSR sensing device;

measuring stress level of the learner by sensing heart rate variability (HRV);

measuring an actual cognitive state of the learner after the task using a questionnaire filled by the learner after performing the task;

creating, by a processor, a Bayesian network framework, wherein the Bayesian network framework includes a plurality of evidence nodes, a plurality of sensor nodes and a plurality of state nodes and wherein the plurality of sensor nodes include the EEG, GSR and HRV parameters;

providing intelligence quotient (IQ) level of the learner and the difficulty level of the task as inputs to the plurality of evidence nodes;

predicting, by the processor, a cognitive state of the learner using results obtained from the plurality of sensor nodes and the inputs provided at the plurality of evidence nodes;

comparing, by the processor, the predicted cognitive state with the actual cognitive state,
wherein if the predicted cognitive state is same as the actual cognitive state then the processor validates the Bayesian network framework, else
the processor resolves a conflict generated due to a difference between the predicted cognitive state and the actual cognitive state by reasoning between the nodes using probabilistic queries.

* * * * *